United States Patent
Teissier et al.

(12)

(10) Patent No.: US 6,274,772 B1
(45) Date of Patent: Aug. 14, 2001

(54) CONTINUOUS PROCESS FOR THE MANUFACTURE OF 3,5,5-TRIMETHYLCYCLOHEXA-3-EN-ONE(β-ISOPHORONE)

(75) Inventors: Rémy Teissier, Francheville; Georges Martino-Gauchi, Chantilly, both of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/598,485

(22) Filed: Jun. 22, 2000

(30) Foreign Application Priority Data

Jun. 22, 1999 (FR) .................................................. 99 07920

(51) Int. Cl.[7] .................................................. C07C 45/67
(52) U.S. Cl. ............................................................ 568/341
(58) Field of Search ............................................... 568/341

(56) References Cited

U.S. PATENT DOCUMENTS 4,845,303 * 7/1989 Bellut .
5,276,197 * 1/1994 Nosberger et al. .
5,907,065 * 5/1999 Krill et al. .

FOREIGN PATENT DOCUMENTS 0 832 871 A1   4/1998   (EP) .
0 842 918 A1   5/1998   (EP) .
2 253 730      7/1995   (FR) .

* cited by examiner

Primary Examiner—Johann Richter
Assistant Examiner—Sikarl A. Witherspoon
(74) Attorney, Agent, or Firm—Millen, White, Zelano & Branigan, P.C.

(57) ABSTRACT

This invention relates to a continuous process for the manufacture of β-isophorone by isomerization under homogeneous catalysis of α-isophorone. The process consists of introducing α-isophorone and a solution of an alkaline hydroxide into a reaction region at a temperature ranging from 150° C. to 216° C., simultaneously removing by distillation a fraction comprising an amount by weight of β-isophorone ranging from 30% to 90%, drawing off the heavy products and then rectifying the fraction removed from the reaction mixture by distillation.

19 Claims, No Drawings

CONTINUOUS PROCESS FOR THE MANUFACTURE OF 3,5,5-TRIMETHYLCYCLOHEXA-3-EN-ONE(β-ISOPHORONE)

FIELD OF THE INVENTION

The invention relates to a continuous process for the manufacture of 3,5,5-trimethylcyclohexa-3-en-1-one, hereinafter β-isophorone, by isomerization of 3,5,5-trimethylcyclohexa-2-en-1-one, hereinafter α-isophorone, in the liquid phase in the presence of a homogeneous catalyst.

BACKGROUND OF THE INVENTION

β-Isophorone is a synthetic intermediate in the manufacture of carotenoids, of vitamins, such as vitamin E, and of pharmaceuticals.

It is also directly involved in syntheses of fragrances and natural products, such as astaxanthin and abscisic acid and derivatives.

β-Isophorone is an isomer of α-isophorone, obtained by trimerization of acetone in alkaline medium, which is distinguished from the latter by the position of the double bond: the double bond is no longer conjugated with the carbonyl, as represented hereinbelow:

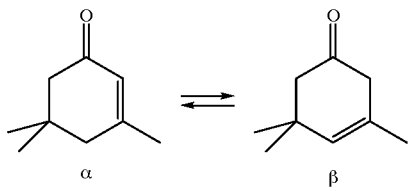

The isomerization of α-isophorone to β-isophorone is an equilibrium deconjugation reaction of the double bond and of the carbonyl and, for this reason, the thermodynamic equilibrium is weighted towards α-isophorone.

Numerous processes for the isomerization of α-isophorone to β-isophorone have been described but exhibit numerous disadvantages, such as high consumption of chemicals (in particular catalysts), mediocre yields or formation of α-isophorone condensation products (heavy products), which results in a rise in the temperature of the reaction mixture,. thus accelerating the formation of heavy products, which destabilize the system.

Patent EP 832,871, Example 7, discloses a process for the preparation of β-isophorone by catalytic isomerization of α-isophorone which consists, in a first step, in continuously extracting from the reaction mixture, by distillation, a primary mixture comprising from 20 to 22% of β-isophorone and in then isolating from this mixture, by distillation, a β-isophorone with a purity equal to approximately 98%. It is found, when proceeding in this way, that a mixture composed of approximately 90% of α-isophorone and 10% of heavy products is collected in the recirculation evaporator. In view of the duration of operation (approximately 15 hours) and of the amount of product collected in the said evaporator (615 g), this corresponds to an hourly production of heavy products of approximately 4 g/h.

In addition, a large amount by weight of catalyst is used: 0.6% with respect to the α-isophorone employed.

If the thermodynamics of the reaction are considered, it is found that the temperature at which isomerization is carried out fixes the concentration of β-isophorone at equilibrium: the higher the temperature, the greater the concentration at equilibrium of β-isophorone. As β-isophorone is more volatile than α-isophorone, the equilibrium can be shifted by distillation of the most volatile product. In addition, β-isophorone, on heating, reverse isomerizes to α-isophorone, even in the absence of catalyst: the kinetics of this thermal reverse isomerization are slow.

It is therefore advantageous to carry out the isomerization at high temperature.

The objective of obtaining pure β-isophorone (β-isophorone/α-isophorone≧2 99%) cannot be achieved in a single column at the isomerization temperature. This is because the β-isophorone/α-isophorone separation requires not only a column with many theoretical plates but also a high reflux ratio. The reflux ratio R is defined as being the ratio of the total amount of condensate obtained at the distillation column top to the amount of product extracted. The increase in the reflux ratio makes it possible to increase the concentration of the β-isophorone extracted up to a certain threshold. This is because a high reflux ratio increases the mean residence time of the β-isophorone in the distillation column, that is to say at high temperature, promoting thermal retrogression.

Thus, a high reflux ratio does not make it possible to produce β-isophorone referred to as pure.

Furthermore, to carry out the isomerization, it is necessary to pass through the intermediate enol or enolate, which are also intermediates in the aldolization/crotonization reaction, which results in the formation of isophorone polycondensates which constitute heavy products, the formation of which is to be prohibited since they represent a loss of isophorone in a process for the manufacture of β-isophorone. The formation of the heavy products is promoted, on the one hand, by the concentration of catalyst and, on the other hand, by the temperature.

Thus, the use of heterogeneous catalysts does not appear to be very favorable as it can increase the concentration of heavy products at the surface of the solid catalyst, which can deactivate the said catalyst.

SUMMARY OF THE INVENTION

A continuous process for the manufacture of 3,5,5-trimethylcyclohexa-3-en-1-one (β-isophorone) by isomerization under homogeneous catalysis of 5 3,5,5-trimethylcyclohexa-2-en-1-one (α-isophorone), obtained by trimerization of acetone in alkaline medium, has now been found, the said process being characterized in that the following stages are carried out:

a) α-isophorone and a solution of an alkaline hydroxide are continuously introduced into a reaction region, b) the reaction mixture is brought to a temperature at least equal to 150° C. and preferably to a temperature ranging from 185° C. to 216° C., c) the following are continuously and simultaneously removed from the said reaction mixture:
1) by distillation, at a temperature between 150° C. and 216° C. and under a pressure ranging from 350 mbar to atmospheric pressure, a fraction comprising an amount by weight of β-isophorone ranging from 30% to 90% and preferably ranging from 50% to 70%; and
2) by drawing off, heavy products, so that their content is at most equal to 7% by weight in the reaction mixture, d) the fraction distilled in c) 1) is rectified continuously and in parallel under reduced pressure at a temperature ranging from 100° C. to 150° C., so as to obtain β-isophorone with a purity as defined by the β-isophorone/α-isophorone ratio of greater than 99%, and, e) the bottoms from the rectification are continuously returned to the reaction region.

According to the present invention, the alkaline hydroxide is NaOH or KOH. It is preferable to use KOH. This alkaline hydroxide can be dissolved in water or an aliphatic alcohol of low molecular weight, such as methanol, ethanol, propanol or isopropanol. Methanol or ethanol is generally used.

According to the present invention, use is made of an amount by weight of alkaline hydroxide at most equal to 0.03% with respect to the α-isophorone introduced into the reaction region.

Use will preferably be made of an amount by weight of alkaline hydroxide ranging from 0.010% to 0.020%.

The reflux ratio for the distillation of the fraction comprising the β-isophorone, the parameter which regulates the concentration of β-isophorone in his fraction, is chosen so as to minimize the thermal retrogression for a maximum β-isophorone purity.

According to the invention, a mixture comprising a percentage by weight of heavy products at most equal to 7%, the remainder being a mixture of α- and β-isophorones, is continuously extracted. These heavy products are composed essentially of dimers and trimers of isophorone and also of catalytic residues. These heavy products can advantageously be introduced into a line for the manufacture α-isophorone by basic catalysis, after the trimerization reaction of acetone and before the neutralization of the basic catalyst.

The continuous process according to the present invention, characterized by continuously drawing off the heavy products, exhibits the advantage, by limiting the concentration of the said heavy products in the boiler, of stabilizing the temperature of the isomerization.

Another advantage of the process of the invention is that it is not necessary to carry out expensive treatment operations on the said heavy products since they can be recycled in a unit for the manufacture of α-isophorone.

The process of the invention also exhibits the advantage of consuming small amounts of catalytic charge.

The examples which follow illustrate the invention:

The equipment used is composed of:

1) an isomerization boiler or reactor which can comprise 300 g of α-isophorone, surmounted by an adiabatic column with a length of 1 m and a diameter equal to 20 mm, comprising a Sulzer EX 20 stacked packing made of 316L stainless steel, and an adiabatic column top with a reflux ratio regulated by a timer;

2) a rectifying column identical to the column surmounting the boiler, the mixture of α- and β-isophorones being introduced into the middle of the said rectifying column.

EXAMPLE 1

In the equipment described hereinabove, 300 g of α-isophorone (Elf Atochem S.A.), comprising 0.02% by weight of KOH (expressed as pure KOH) dissolved beforehand in methanol at a concentration by weight of KOH of approximately 20%, are introduced into the reactor.

The mixture is brought to boiling under a pressure of 600 mbar. Reflux begins at 195° C. and stabilizes at 196° C. The top temperature stabilizes at approximately 166° C. The timer is then started, the reflux ratio being adjusted to 80.

At the same time, the pump for introducing the reactants into the isomerization reactor at a throughput of 16.5 g/h of α-isophorone, comprising 0.004% by weight of KOH (expressed as pure KOH) dissolved in methanol, and the pump for drawing off from the isomerization reactor, regulated at a throughput of 1.5 g/h, are started.

After operating for 4 hours, the top temperature stabilizes at between 175 and 176° C. and 15 g/h of a β-isophorone/α-isophorone mixture with a mean composition of 72/28 are produced.

This equipment is thus operated for 210 hours.

The temperature of the isomerization reactor is stable between 196° C. and 197° C. The top temperature is constant and equal to 176–177° C. The composition and the throughput of the mixture extracted at the top are constant: respectively 72% of β-isophorone on average for a variation interval from 70% to 75% and 14.5 g/h on average for a variation interval from 14 g/h to 15 g/h.

The productivity of pure β-isophorone is 10 g/h on average.

The composition of the material drawn off continuously from the isomerization reactor is stable and comprises, from the eighth hour, 2% of heavy products (measured by gas chromatography), 97% of α- and β-isophorones and 1% of various products. 3605 g of α-isophorone are introduced over 210 h. 3036 g of 72/28 β-isophorone/α-isophorone mixture are produced, i.e. 2185 g of β-isophorone. 311 g of isophorone comprising 2% of heavy products and 1% of various products are drawn off from the isomerization reactor, which corresponds to a loss of 0.2% with respect to the isophorone introduced. This corresponds to an hourly production of heavy products of 0.03 g/h.

The top flow, after storage in a holding tank, is conveyed to the middle of the rectifying column, which operates under a pressure of 100 mbar. The top temperature stabilizes at 110° C., while the column bottom temperature stabilizes at 135° C. The top fraction assays a β-isophorone purity of 99.2%. The material drawn off from the bottom of the column assays between 6% and 4% of β-isophorone. The reflux ratio is 7. 2140 g of 99% β-isophorone are recovered at the top, i.e. 98% of the β-isophorone introduced into the rectifying column. 896 g of α-isophorone comprising 5% on average of β-isophorone are recovered at the bottom.

This mixture is recycled, either directly to the isomerization reactor or to the mixer for mixing commercial isophorone with the catalyst.

EXAMPLE 2

After operating for 210 hours, the setting for the reflux ratio of the distillation column, the boiler of which is the isomerization reactor, is modified by being brought to 20 and this operating arrangement is maintained for an additional 24 hours.

A fraction assaying 20% by weight of β-isophorone is obtained at the top with a throughput of 52 g/h. The top temperature stabilizes at 190° C. while the temperature of the isomerization reactor remains stable at 196° C.

The throughput for introduction of the α-isophorone is regulated so as to maintain the same mass in the isomerization reactor: introduction throughput=53.5 g/h at a concentration of 0.0005% of KOH in the isophorone (4-fold dilution of the solution used in Example 1). The throughput for drawing off from the isomerization reactor is maintained at 1.5 g/h and the analysis of this flow remains stable: 97% approximately of isophorone, 2% of heavy products and 1% of various products.

The β-isophorone productivity is 10.4 g/h on average, that is to say almost the same as that in Example 1.

240 g of β-isophorone with a purity of 99.2% are produced over 24 h.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/07.920, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

CROSS-REFERENCE TO RELATED APPLICATION

This application is related to Applicants' concurrently filed application Attorney Docket No. ATOCM 188, entitled "Continuous Process For The Manufacture Of 3,5,5-Trimethylcyclohexa-3-En-1-One (β-Isophorone)", based on French Application 99/07.919 filed on Jun. 22, 1999.

What is claimed is:

1. A continuous process for the manufacture of 3,5,5-trimethyl-cyclohexa-3-en-1-one (β-isophorone) by isomerization under homogeneous catalysis of 3,5,5-trimethylcyclohexa-2-en-1-one (α-isophorone), obtained by trimerization of acetone in an alkaline medium, said process comprising:
   a) continuously introducing α-isophorone and a solution of an alkaline hydroxide into a reaction region,
   b) heating the reaction mixture,
   c) continuously and simultaneously removing from said reaction mixture:
      1) by distillation, a fraction comprising an amount by weight of β-isophorone ranging from 30% to 90%; and
      2) drawing off, heavy products, so that their content is at most equal to 7% by weight in the reaction mixture,
   d) rectifying the fraction distilled in c) 1) so as to obtain β-isophorone with a purity as defined by the β-isophorone/α-isophorone ratio of greater than 99% and,
   e) continuously returning the bottoms from the rectification to the reaction region.

2. A process according to claim 1, wherein in b), the reaction mixture is brought to a temperature ranging from 185° C. to 216° C.

3. A process according to claim 1, wherein in c) 1), the distilled fraction comprises an amount by weight of α-isophorone ranging from 50% to 70%.

4. A process according to claim 1, wherein the alkaline hydroxide is KOH.

5. A process according to claim 1, wherein the alkaline hydroxide is dissolved in an aliphatic alcohol of low molecular weight.

6. A process according to claim 5, wherein the aliphatic alcohol of low molecular weight is methanol or ethanol.

7. A process according to claim 1, comprising using an amount by weight of alkaline hydroxide at most equal to 0.03% with respect to the α-isophorone employed (introduced into the reaction region).

8. A process according to claim 7, comprising using an amount by weight of alkaline hydroxide ranging from 0.010% to 0.020% with respect to the α-isophorone employed.

9. A process according to claim 1, wherein the heavy products drawn off from the isomerization reactor, in c) 2), are recycled in a line for the manufacture of α-isophorone.

10. A process according to claim 9, wherein the heavy products are introduced into a line for the manufacture of α-isophorone after the trimerization reaction of the acetone and before the neutralization of the basic catalyst.

11. A process according to claim 2, wherein in c) 1), the distilled fraction comprises an amount by weight of β-isophorone ranging from 50% to 70%.

12. A process according to claim 11, wherein use is made of an amount by weight of alkaline hydroxide at most equal to 0.03% with respect to the α-isophorone employed (introduced into the reaction region).

13. A process according to claim 11, wherein use is made of an amount by weight of alkaline hydroxide ranging from 0.010% to 0.020% with respect to the α-isophorone employed.

14. A process according to claim 1, wherein in b), the reaction mixture is brought to a temperature at least equal to 150° C.

15. A continuous process for the manufacture of 3,5,5-trimethyl-cyclohexa-3-en-1-one (β-isophorone) by isomerization under homogeneous catalysis of 3,5,5-trimethylcyclohexa-2-en-1-one (α-isophorone) obtained by trimerization of acetone in an alkaline medium, said process comprising continuously and simultaneously introducing α-isophorone and alkaline hydroxide into a reaction region to produce β-isophorone.

16. The method according to claim 14, wherein the alkaline hydroxide is KOH.

17. The process according to claim 1, wherein in b) the reaction mixture is brought to a temperature at least equal to 150° C.

18. The process according to claim 1, wherein in c) 1) the distillation is at a temperature between 150° C. and 216° C. and under a pressure ranging from 350 mbar to atmospheric pressure.

19. The process according to claim 1, wherein in d) the fraction distilled in c) 1) is rectified continuously and in parallel under reduced pressure at a temperature ranging from 100° C. to 150° C.

* * * * *